United States Patent [19]

Holmes

[11] Patent Number: 5,417,701
[45] Date of Patent: May 23, 1995

[54] SURGICAL INSTRUMENT WITH MAGNETIC NEEDLE HOLDER

[75] Inventor: Russell P. Holmes, Boston, Mass.

[73] Assignee: Holmed Corporation, So. Easton, Mass.

[21] Appl. No.: 39,884

[22] Filed: Mar. 30, 1993

[51] Int. Cl.⁶ ............................................. A61B 17/00
[52] U.S. Cl. .................................. 606/148; 606/147; 606/207; 81/418
[58] Field of Search ............... 606/139, 144, 147, 148, 606/106, 205, 207; 81/125, 186, 421, 418; 269/276

[56] References Cited

U.S. PATENT DOCUMENTS

| | | |
|---|---|---|
| 3,160,157 | 3/1962 | Chisman . |
| 3,349,772 | 10/1967 | Rygg . |
| 3,370,490 | 2/1968 | Feldman et al. ........................ 81/125 |
| 4,315,447 | 2/1982 | Tartaglia et al. ...................... 81/421 |
| 4,597,390 | 7/1986 | Mulhollan et al. . |
| 4,760,848 | 8/1988 | Hasson . |
| 4,823,650 | 4/1989 | Tuttle .................. 81/124.2 |
| 4,949,717 | 8/1990 | Shaw .................. 606/147 |
| 4,961,742 | 10/1990 | Torre .................. 606/208 |
| 5,059,207 | 10/1991 | Shah . |
| 5,100,421 | 3/1992 | Christoudias . |
| 5,147,373 | 9/1992 | Ferzli . |
| 5,152,769 | 10/1992 | Baber . |
| 5,178,048 | 1/1993 | Matechuk ................ 81/125 |
| 5,180,385 | 1/1993 | Sontag . |
| 5,201,744 | 4/1993 | Jones .................... 606/139 |
| 5,222,967 | 6/1993 | Burkhart ............... 606/147 |
| 5,243,883 | 9/1993 | Savage .................. 269/276 |
| 5,257,999 | 11/1993 | Slanetz, Jr. ........... 606/147 |

Primary Examiner—Stephen C. Pellegrino
Assistant Examiner—Jeffrey A. Schmidt
Attorney, Agent, or Firm—Cesari and McKenna

[57] ABSTRACT

A suturing instrument for use in endoscopic surgery includes at one end of an elongated barrel a pair of jaws to grasp and release a needle. Within one of the jaws a recessed magnet properly positions, orients and holds the needle relative to the long axis of the barrel. In a preferred embodiment of an instrument with the magnet embedded in a lower jaw, the instrument includes a wire, which moves in parallel with an upper jaw as that jaw opens and closes, to push the needle out of the contact with the magnet in the lower jaw. The wire fits within a recess, and lies beneath the needle when the needle is in position and the jaws are closed. An alternative embodiment of the instrument includes in one of the jaws a magnet which is magnetized across the diameter. This magnet is oriented, relative to a long axis of the elongated barrel, such that the poles are perpendicular to the axis. A needle which has a magnet embedded in the suture end, or has the suture end which is coated with a material which is more magnetically permeable than the needle may be used with the instrument, to direct the needle to a particular position on the magnet.

10 Claims, 2 Drawing Sheets

SURGICAL INSTRUMENT WITH MAGNETIC NEEDLE HOLDER

FIELD OF INVENTION

The invention relates generally to surgical instruments and, more particularly, to surgical instruments for use in endoscopic surgery.

BACKGROUND OF INVENTION

Endoscopic surgery is performed through a plurality of relatively small incisions, using special surgical instruments and a microscope with a tiny camera. This type of surgery tends to reduce the length of postsurgery recovery, because the small incisions typically heal faster than do the larger incisions required in other types of surgery.

To perform endoscopic surgery, the surgeon makes a number of small incisions in the body, inserts into the incisions the surgical instruments and the microscope into the abdominal cavity through the incisions and manipulates the instruments while observing on a video screen the images transmitted by the camera.

An instrument designed for endoscopic surgery includes a thin, elongated barrel with a tool for cutting, suturing or the like at one end and a control handle for manipulating the tool at the other end. The tool is inserted into the body through one of the small incisions and the surgeon manipulates the tool by means of the handle.

A tool currently used for suturing during endoscopic surgery includes at one end movable jaws, for grasping and releasing a needle, and at the opposite end a scissor-like control handle, which is used to open and close the jaws and to move the needle. The surgeon grasps the needle by closing the jaws around it. She then inserts the needle into and through the tissue requiring suturing and opens the jaws to release the needle. Next, she uses the same instrument or another, similar tool to grasp the needle and pull it through the tissue. She then repeats the movements, as necessary, to complete the suturing procedure.

Throughout the suturing procedure, the surgeon has to release and re-grasp the needle a number of times. Each time the surgeon re-grasps the needle, she must be sure that it is positioned and oriented correctly within the jaws, so that she is then ready to insert the needle into and through the tissue to make another stitch. Accordingly, the surgeon must first determine the position and orientation of the needle in the jaws. This is difficult, because her only view of the needle and the instrument is via a two-dimensional image transmitted by the camera. Next, she must adjust the needle within the jaws, as necessary, which is difficult because the jaws only open and close.

Further, the surgeon must be sure that she does not drop the needle, since the needle may be difficult to locate in the transmitted image. Once a dropped needle is located, picking it up, particularly with the suturing instrument, is a challenge. Often, a special instrument, and another hand to manipulate the instrument, are required.

SUMMARY

A suturing instrument embodying the invention uses a magnet to properly position, orient and hold a needle within its jaws. The magnet is embedded in one of the jaws and when the jaws are near the needle, the magnet attracts the needle to it, causing the needle to move to a predetermined position on the jaw containing the magnet. The surgeon may then have to push the needle across the magnet, to further expose the sharpened end of the needle. Such an adjustment is easily made and, since the needle remains in contact with the magnet, the needle does not drop out of the jaws.

With the needle in the desired position and orientation, the surgeon manipulates the instrument to insert the needle into, and part way through the tissue to be sutured. She then uses a second, similar instrument to grasp the needle and pull it the rest of the way through the tissue. This second instrument may include a magnet, which is preferably of lesser strength than the magnet in the first instrument. When this second instrument pulls the needle out of the tissue, the included magnet draws the needle into proper position within its jaws and holds the needle in this position until the needle is transferred to the first instrument. To transfer the needle, the two instruments are brought together, both sets of jaws are opened, and because of the greater strength of the magnet in the first instrument, the needle moves from its position in the second set of jaws to its previous position in the first set of jaws. The surgeon then re-grasps the needle by closing the jaws of the first instrument around it, pushes the needle across the magnet, as necessary, to further expose the sharpened end, and continues the suturing procedure.

Alternatively, the surgeon may use the same instrument to re-grasp the needle and pull it through the tissue, with the needle properly positioning itself within the jaws once it is free of the tissue.

Suturing instruments for use with various types of needles, for example, straight needles, curved needles, ski needles and so forth, include magnets which are either axially magnetized or magnetized across their diameters, with poles which are positioned at various angles relative to the long axis of the barrel. Similarly, instruments for a particular surgical procedure, or for use by a particular surgeon, may have magnets which are moved to various locations on either the upper jaw or the lower or rotated relative to the long axis of the barrel, as necessary to position and orient the needles as desired.

To eliminate the need to adjust the position of the needle on the magnet, the suture end of the needle may be coated with a material which is more magnetically permeable than the needle, or the needle may include a magnet in the suture end. The suture end of the needle is then drawn into contact with the magnet within the jaws of the instrument, such that the sharpened end of the needle is appropriately exposed.

DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
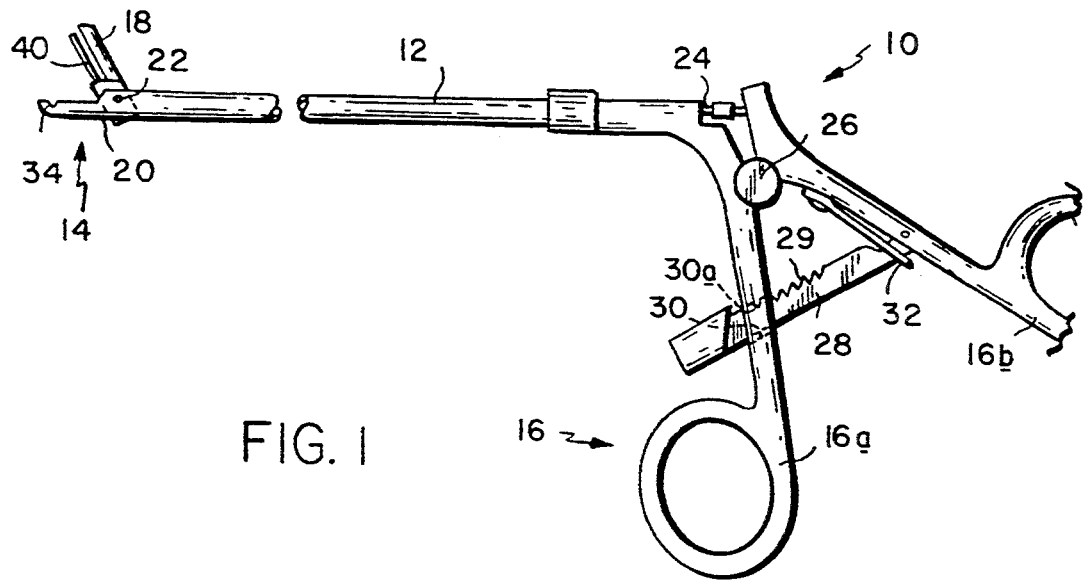
FIG. 1 is a side view of a surgical instrument constructed in accordance with the invention, illustrating a fully-opened jaw and a scissor-like control mechanism.

FIG. 1 depicts an instrument 10 which includes an elongated barrel 12, that has at one end 14 a pair of jaws 18 and 20 and at the opposite end a scissor-like control mechanism 16. The upper jaw 18 is movable and the lower jaw 20 is stationary relative to the barrel. Specifically, the jaw 18 rotates about pivot 22, to open and close the jaws. The control mechanism 16 controls the pivotal movement of the jaw 18, via a rod 24, which runs between them through the interior of barrel 12.

Figure 2:
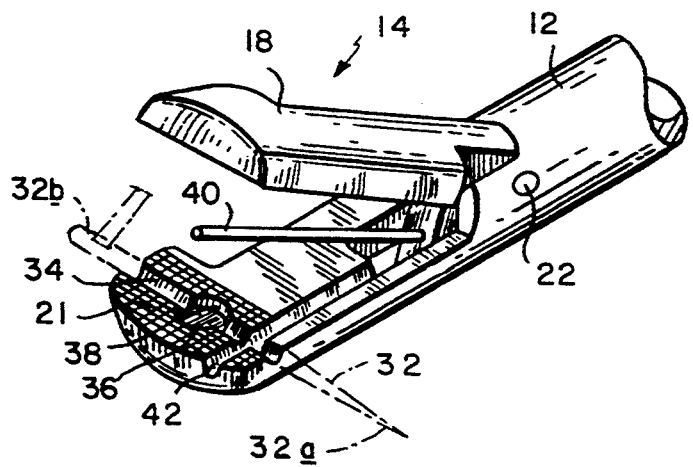
FIG. 2 is an enlarged front view of the jaw of FIG. 1.

The jaws 18 and 20, which are depicted in more detail in FIG. 2, close and open to grasp and release a needle 32 which is properly positioned and oriented by a magnet 36 disposed beneath a transverse groove 34 in the jaw 18. When the jaws 18 and 20 are closed, teeth 19 and 21 (FIG. 3) on the upper and lower jaws 18 and 20, respectively, engage to help retain the needle 32 in the groove 34.

The hand piece 16b rotates about a pivot 26 to move the rod 24, and at the other end of the rod, rotate the jaw 18. The hand piece 16b can be retained in a desired position by a notched ratchet 28, which is attached to the hand piece 16b and extends through a slot 30 in hand piece 16a. The notches 29 of the ratchet 28 mesh with an edge 30a of the slot, to hold the hand piece 16b in place. In order to move the hand piece 16b, the user depresses the ratchet 28, to disengage the bar from the edge 30a of the slot. To prevent accidental release of the hand piece 6b, a spring 32 provides resistance against the downward movement of the ratchet 28.

Referring to FIG. 2, the magnet 36, which is retained in a recess 38 in the lower jaw 20, draws the needle 32 laterally toward the groove 34, and pulls the needle into the groove to properly orient the needle relative to the barrel 12.

Figure 3:
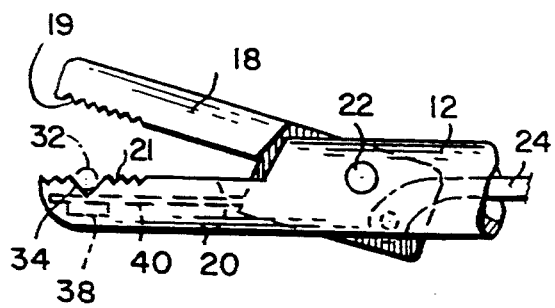
FIG. 3 is a side view of the jaw of FIG. 1, in a semi-open position.
Figure 4:
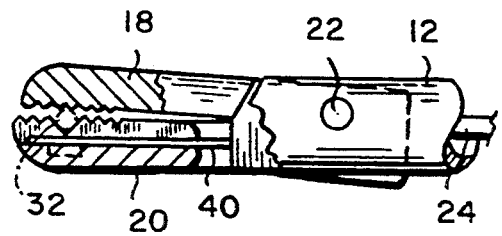
FIG. 4 is a side view of the jaw of FIG. 1, in a closed position.

A wire 40, which is attached to and moves in parallel with the jaw 18, operates to push the needle out of the groove 34 as the jaws open to release the needle. When the jaws are closed around the needle, the wire lies beneath the needle 32 in recess 42, as depicted in FIGS. 3 and 4. To grasp the needle 32 properly, the jaws must be partially closed, with the wire 40 in the recess 42, before the jaws are placed around the needle. As the jaws later open to release the needle, the wire rises out of its recess 42 and essentially pushes the needle out of its groove 34, and thus, out of contract with the recessed magnet 36. While this wire is not necessary for the proper operation of the instrument, it does allow the surgeon to pull the instrument smoothly away from the needle, when the needle is inserted into tissue. Without the wire, the attraction between the magnet and the needle may be strong enough to require that the surgeon move the instrument out of contact with the needle relatively quickly, to avoid inadvertent repositioning of the needle within the tissue.

If the magnet 36 is magnetized across its diameter, that is, has both its north pole and its south pole facing in an upward direction, the needle positions itself directly across the poles. Accordingly, the lower jaw 20 need not include the transverse groove 34.

The included magnet 36, which may be axially magnetized, with either its north pole or its south pole facing upward, or magnetized across its diameter, properly positions and orients a needle within the jaws 14. The surgeon need only bring the instrument in close proximity to the needle, and the magnet attracts the needle to the desired lateral position and directs the needle into the desired orientation by pulling it into the transverse groove. The surgeon should approach the needle from a particular end, i.e., either the suture end or the sharpened end, depending on whether the instrument is being used to insert the needle into the tissue or pull the needle from the tissue. The surgeon later pushes the needle across the magnet, as necessary, to expose the sharpened end.

The magnet 36 not only attracts the needle to its proper position within the jaws, it retains the needle in position within the jaws, such that the needle will not easily drop out. Thus the surgeon is not faced with trying to locate a dropped needle by finding it within the two-dimensional image transmitted by the camera.

To perform a suturing procedure, a surgeon grasps a needle 32 with the suturing instrument 10, and guides the needle, which is properly positioned within the jaws 14 by the magnet 36, through the tissue. If the surgeon uses two suturing instruments, she uses the second instrument to grasp the sharpened end of the needle, which is now sticking out of the other side of the tissue, and pull the needle through the tissue. If this second instrument includes a magnet, she opens the jaws of the instrument slightly, to allow the needle to position itself within the jaws. Preferably, the second instrument includes a magnet which is somewhat weaker than the magnet included in the first instrument. The surgeon transfers the needle back to the first instrument by bringing the first instrument close to the second instrument, opening the two sets of jaws and allowing the needle to move from the weaker magnet to the stronger magnet.

If the second instrument does not include a magnet, the surgeon follows the same procedure to transfer the needle, however, she must be careful not to allow the needle to fall out of the jaws of the second instrument.

The two instruments may, respectively, include axially magnetized magnets with opposite poles facing in the upward direction, that is, one instrument with a magnet with an upwardly facing north pole and the other instrument with a magnet with an upwardly facing south pole. Since the magnets tend to magnetize the needle, the needle inserted into the tissue by an instrument which includes an upwardly facing north pole has a magnetic north pole at its sharpened end and a magnetic south pole at its suture end. The second instrument, which grasps the needle by its sharpened end, maintains the magnetic orientation of the needle, since the included magnet has an upwardly facing south pole. When the needle is later transferred to the first instrument its suture end, which is a magnetic south pole, is drawn directly into contact with the magnet. Accordingly, the sharpened end of the needle extends out from the jaw such that only a minor re-adjustment, if any, is required before the needle is ready for re-insertion.

If the surgeon uses a single instrument to perform the suturing procedure, she inserts the needle into the tissue, releases the needle and re-grasps the exposed sharpened end of the needle. After pulling the needle from the tissue, the surgeon opens the jaws slightly, to allow the needle to position itself relative to the magnet. She then pushes the needle across the magnet to expose the sharpened end of the needle, as necessary, and again inserts the needle into the tissue.

The needle 32 may have, at the suture end, an embedded magnet or a thin coating of material which is more magnetically permeable than the needle. Accordingly, the suture end of the needle is drawn directly to the magnet, such that the sharpened end is appropriately exposed. This eliminates the need to adjust the position of the needle on the magnet, that is, to push the needle across the magnet to expose further the sharpened end.

Figure 5:
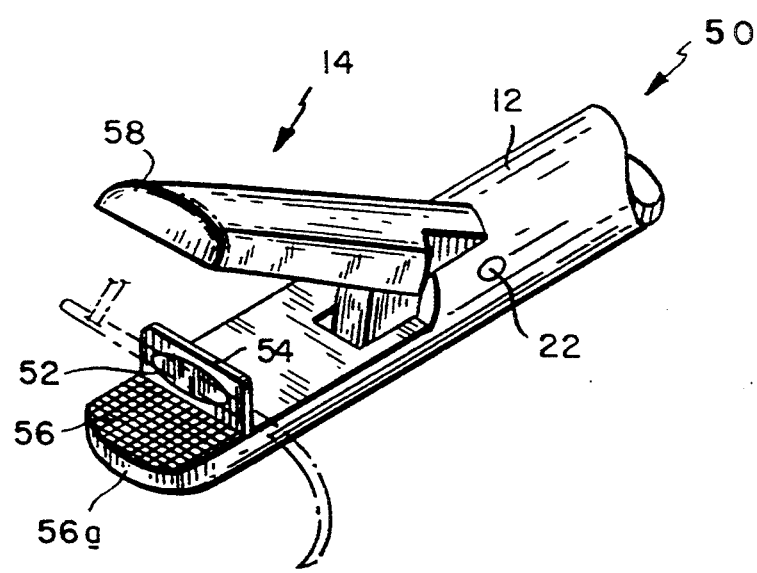
FIG. 5 is a front view of an alternative embodiment of the invention.

FIG. 5 depicts an alternative embodiment of the instrument 10 of FIG. 1, for use with curved needles. Those elements of instrument 50 that are identical to the instrument 10 (FIGS. 1–4) are denoted by using the same reference numerals used in FIGS. 1–4. A magnet 52, which is magnetized across the diameter such that its north and south poles face in the same direction, is embedded in a protrusion 54 which is part of the lower jaw 56. The magnet 52 draws the curved needle to it such that the sharpened end of the needle faces either directly up or directly down. The magnet 52 thus positions and orients the needle properly for suturing. The end 56a of the lower jaw 56 is narrower than the end of the lower jaw 20 of the instrument 10 (FIG. 2), to accommodate the curve of the needle. Accordingly, the lower jaw 56 does not include the club end of jaw 20. Further, the upper jaw 58 is hollowed to accommodate the protrusion.

The foregoing description has been limited to specific embodiments of this invention. It will be apparent, however, that variations and modifications may be made to the invention, with the attainment of some or all of its advantages. Therefore, it is the object of the appended claims to cover all such variations and modifications as come within the true spirit and scope of the invention.

I claim:

1. A surgical suturing instrument for use with a needle, the suturing instrument including:
   A. an elongated barrel having a first end and a second end;
   B. a pair of jaws attached to the second end of said barrel, the pair of jaws consisting of a first jaw and an opposing second jaw;
   C. control means attached to the first end of said barrel, the control means manipulating at least one of the first and second jaws to open and close them;
   D. a groove means for orienting the needle to a predetermined angle relative to a longitudinal axis of said barrel; and
   E. a magnet embedded in one of the first or the second jaws adjacent the groove means for attracting the needle into the grove and retaining the needle between said pair of jaws.

2. The surgical suturing instrument of claim 1, wherein the jaw in which the magnet is embedded includes in a surface facing the opposing jaw a recess within which said magnet is positioned, said recess being deep enough to position said magnet wholly beneath the surface of the jaw.

3. The surgical suturing instrument of claim 1, wherein said magnet is positioned such that one pole faces the opposing jaw.

4. The surgical suturing instrument of claim 1, wherein said control means moves one of said jaws to open and close said pair of jaws.

5. The surgical suturing instrument of claim 4, wherein said pair of jaws further includes a wire which is connected to and moves with the jaw which is moved by said control means, said wire fitting between the needle and one of the jaws and displacing the needle when said pair of jaws are opened more than a predetermined amount.

6. The surgical suturing instrument of claim 1, wherein said groove means is oriented relative to the longitudinal axis of the barrel to orient the needle at the predetermined angle.

7. The surgical suturing instrument of claim 6, wherein said groove is perpendicular to the length of said barrel.

8. A surgical suturing instrument for use with a needle, the suturing instrument including:
   A. an elongated barrel having a first end and a second end;
   B. a pair of jaws attached to the second end of said barrel, the pair of jaws consisting of a first jaw and an opposing second jaw;
   C. control means attached to the first end of said barrel, the control means manipulating at least one of the first and second jaws to open and close them; and
   D. a magnet embedded in one of the first or the second jaws, the magnet being cylindrical and magnetized across its diameter such that two poles of the magnet are on opposing sides of the diameter, said magnet being positioned within the jaw such that the magnetic flux from the poles is shielded by the jaw in all but the upwardly direction, said magnet attracting the needle to it, positioning and orienting the needle across the poles, and retaining the needle between said pair of jaws.

9. The surgical suturing instrument of claim 8, wherein the jaw into which said magnet is embedded includes a protrusion that extends toward the opposing jaw, said protrusion housing said magnet, with at least one pole of said magnet facing away from the second end of the barrel.

10. The surgical suturing instrument of claim 8, wherein said magnet is oriented such that its longitudinal axis is perpendicular to the longitudinal axis of the barrel.

* * * * *